(12) United States Patent
Ikeda et al.

(10) Patent No.: US 8,933,420 B2
(45) Date of Patent: Jan. 13, 2015

(54) PARTICLE BEAM THERAPY SYSTEM

(75) Inventors: Masahiro Ikeda, Chiyoda-ku (JP);
Hisashi Harada, Chiyoda-ku (JP);
Kazushi Hanakawa, Chiyoda-ku (JP);
Toshihiro Otani, Chiyoda-ku (JP);
Tadashi Katayose, Chiyoda-ku (JP);
Taizo Honda, Chiyoda-ku (JP); Yukiko Yamada, Chiyoda-ku (JP); Yuehu Pu, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/240,197

(22) PCT Filed: Nov. 2, 2011

(86) PCT No.: PCT/JP2011/075272
§ 371 (c)(1),
(2), (4) Date: Feb. 21, 2014

(87) PCT Pub. No.: WO2013/065139
PCT Pub. Date: May 10, 2013

(65) Prior Publication Data
US 2014/0187847 A1    Jul. 3, 2014

(51) Int. Cl.
*A61N 5/10* (2006.01)

(52) U.S. Cl.
CPC ............ *A61N 5/1077* (2013.01); *A61N 5/1049* (2013.01); *A61N 5/1069* (2013.01);
(Continued)

(58) Field of Classification Search
CPC ................. A61N 5/1049; A61N 2005/1087; A61B 6/0457; A61B 5/0064; A61B 6/0407; A61B 6/0442; G05B 2219/45117; G21K 1/04; G21K 1/046; G21K 1/093; G21K 1/10

USPC ........... 378/65, 117, 119, 121, 124, 137, 152, 378/196, 197, 209, 41, 64; 600/1, 407, 427; 250/396 R, 398, 492.3, 491.1, 492.1, 250/505.1
See application file for complete search history.

(56) References Cited

U.S. PATENT DOCUMENTS 7,008,105 B2 * 3/2006 Amann et al. ................ 378/209
8,488,741 B2 * 7/2013 Ein-Gal ........................ 378/117
(Continued)

FOREIGN PATENT DOCUMENTS

JP    63-119779 A    5/1988
JP    2004-097646 A    4/2004
(Continued)

OTHER PUBLICATIONS

Weber et al. "Comparison of Carbon Ions Versus Protons", The Cancer Journal, vol. 14, No. 4, Jul./Aug. 2009.*
(Continued)

*Primary Examiner* — Michael Logie
(74) *Attorney, Agent, or Firm* — Buchanan Ingersoll & Rooney PC

(57) ABSTRACT

A particle beam therapy system comprising a treatment table, a treatment table control unit and an irradiation control unit configured to output an instruction for controlling the treatment table control unit, an accelerator and a scanning electromagnet, wherein after the treatment table control unit controls the treatment table so as for a patient isocenter which is reference position of an affected area of a patient to move to a position of an irradiation isocenter which is set at a position which is closer to an irradiation nozzle than an equipment isocenter which is reference of positional relation of the irradiation nozzle and the treatment table, the irradiation control unit outputs an instruction for irradiating the patient with a particle beam.

4 Claims, 9 Drawing Sheets

(52) U.S. Cl.
CPC .............................. *A61N 2005/1087* (2013.01)
USPC .................... 250/491.1; 250/396 R; 250/398;
250/492.3; 250/492.1; 250/505.1; 600/1;
600/407; 600/427; 378/65; 378/117; 378/119;
378/121; 378/209

(56) References Cited

U.S. PATENT DOCUMENTS

| | | | |
|---|---|---|---|
| 2003/0083562 A1* | 5/2003 | Bani-Hashemi et al. ..... | 600/407 |
| 2004/0170254 A1 | 9/2004 | Gregerson et al. | |
| 2004/0264640 A1* | 12/2004 | Myles .............................. | 378/65 |
| 2005/0218341 A1* | 10/2005 | Saracen et al. ............. | 250/491.1 |
| 2006/0017022 A1* | 1/2006 | Rigney et al. .............. | 250/497.1 |
| 2007/0003007 A1 | 1/2007 | Carrano et al. | |
| 2009/0003522 A1* | 1/2009 | Chien et al. ...................... | 378/65 |
| 2010/0181494 A1* | 7/2010 | Mattern ........................ | 250/398 |
| 2011/0121197 A1* | 5/2011 | Maeda et al. ............ | 250/453.11 |
| 2011/0218429 A1* | 9/2011 | Harada et al. ................. | 600/427 |
| 2013/0090514 A1* | 4/2013 | Fadler .............................. | 600/1 |
| 2013/0274538 A1* | 10/2013 | Yamada et al. .................. | 600/1 |

FOREIGN PATENT DOCUMENTS

| | | |
|---|---|---|
| JP | 2005-536288 A | 12/2005 |
| JP | 2007-268035 A | 10/2007 |
| JP | 2008-544833 A | 12/2008 |
| WO | WO 2010/122662 A1 | 10/2010 |

OTHER PUBLICATIONS

International Search Report (PCT/ISA/210) mailed on Dec. 6, 2011, by the Japanese Patent Office as the International Searching Authority for International Application No. PCT/JP2011/075272.

\* cited by examiner

PARTICLE BEAM THERAPY SYSTEM

TECHNICAL FIELD

This invention relates to particle beam therapy system in which a particle beam is applied such as performing cancer treatment by irradiating a particle beam.

BACKGROUND ART

Irradiation method of particle beam therapy system is divided broadly into two methods. That is, a broad irradiation method in which a beam is irradiated into whole of patient's affected area simultaneously and a scanning irradiation method in which a beam is scanned and irradiated. A scanning irradiation method includes a spot scanning irradiation method and a raster scanning irradiation method, however, in this specification, these methods will be referred to collectively as scanning irradiation methods. In order to realize a scanning irradiation method, equipment and controlling methods which are suited for the irradiation methods are required. It is necessary to devise an end from which a particle beam is actually irradiated so as to realize a scanning irradiation method. An end for irradiating a particle beam is referred to as irradiation system, irradiation field forming apparatus, irradiation head, irradiation nozzle, etc.

Regarding irradiation systems for realizing scanning irradiation methods, in order to increase irradiation position accuracy of an affected area of a patient, it is necessary to irradiate a beam having a small beam size. On the other hand, when a beam travels in the atmosphere a size of beam is increased by scattering. Therefore, a configuration of system in which scattering of a beam is suppressed, a part in which a vacuum region or a region of gas such as helium which is lighter than air is secured so as to decrease a beam size is proposed (for example, Patent Document 1). In this specification, a part, in which a vacuum region or a gas region is secured, will be referred to as a duct. Further, in a duct, a part where a particle beam passes will be referred to as a window, and in this specification, a window which is provided in the most downstream of a particle beam track will be referred to as a beam outlet window.

An irradiation nozzle of a particle beam therapy system for realizing a scanning irradiation method includes a vacuum duct for securing a vacuum region, a window where a particle beam passes in a vacuum duct (beam outlet window), a beam scanning apparatus for scanning a particle beam, a beam position monitor for monitoring abeam dose, and a dose monitor for monitoring abeam dose, etc.

When a beam which travels in a straight line hits an obstacle, scattering is generated, and the beam propagates with a certain spread. The spread refers to as a scattering angle, and is indicated as θ (radian). A diameter of a beam spot which is away from a distance of r from an obstacle is approximately rθ. In an irradiation nozzle of a scanning irradiation method, a window which is provided more downstream than a scanning electromagnet or a beam position monitor corresponds to an obstacle. That is, a particle beam is scattered at a part of the window, and then the particle beam propagates with a certain spread.

According to conventional technology, an obstacle which is a factor of beam scattering is positioned away from an isocenter which is an irradiation point, that is, a distance of r is large, therefore, a beam spot diameter is large. Consequently, a beam size which is not small enough for performing practical scanning irradiation method could not be obtained.

In order to solve the above-mentioned problem, Patent Document 2 discloses a configuration, that is, by making a vacuum duct to be expandable, a member, which is a factor of scattering including a beam outlet window which is provided at an end of a vacuum duct, a beam position monitor, a dose monitor, etc., is approached to a patient and a particle beam is irradiated onto the patient.

PRIOR ART REFERENCE

Patent Document

[Patent Document 1]
Japanese Patent Application Laid-Open JP2007-268035A
[Patent Document 2]
International Publication WO2010/122662

DISCLOSURE OF THE INVENTION

Problems to be Solved by the Invention

According to the configuration which is disclosed by Patent Document 2, enlargement of a beam size in an affected area which is an irradiation object is suppressed, and a scanning irradiation with a beam having a small size can be performed. However, in a case where an expandable vacuum duct is formed of a bellow in the way which is disclosed by Patent Document 2, a stroke of a bellows which is not crushed by atmospheric pressure is small. Alternatively, it is necessary to use a bellows which is extremely expensive.

In order to solve the above-mentioned problems, this invention is made. This invention aims to provide particle beam therapy system of a scanning irradiation method in which an expandable vacuum duct is not used, a particle beam can be irradiated with a fixed length irradiation nozzle, while enlargement of a beam size is suppressed, and an irradiation with high accuracy can be performed.

Means for Solving the Problems

Particle beam therapy system according to this invention comprises an accelerator configured to accelerate a charged particle beam so as to extract a particle beam, a vacuum duct configured to transport the particle beam which is extracted from the accelerator, an irradiation nozzle which comprises a scanning electromagnet which is provided at the downstream side of the vacuum duct to deflect the particle beam, which travels in the vacuum duct, perpendicular to the direction of travelling so as to scan a patient's affected area which is an irradiation object and a beam outlet window from which the particle beam comes to the atmosphere, a treatment table configured to place a patient, a treatment table control unit configured to control a position of the treatment table, and an irradiation control unit configured to output instructions for controlling the treatment table control unit, the accelerator and the scanning electromagnet, wherein after the treatment table control unit controls the treatment table so as to move a patient isocenter which is a reference position of an affected area of the patient to a position of an irradiation isocenter which is set at a position closer to the irradiation nozzle than an equipment isocenter which is a reference of positional relationship of the irradiation nozzle and the treatment table, the irradiation control unit outputs instructions for irradiating a patient with the particle beam.

Advantage of the Invention

Particle beam therapy system for realizing a scanning irradiation method, in which a particle beam can be irradiated with a fixed length irradiation nozzle, while enlargement of a beam size is suppressed, and an irradiation with high accuracy can be performed, can be obtained.

EMBODIMENTS FOR CARRYING OUT THE INVENTION

Embodiment 1

Figure 1:
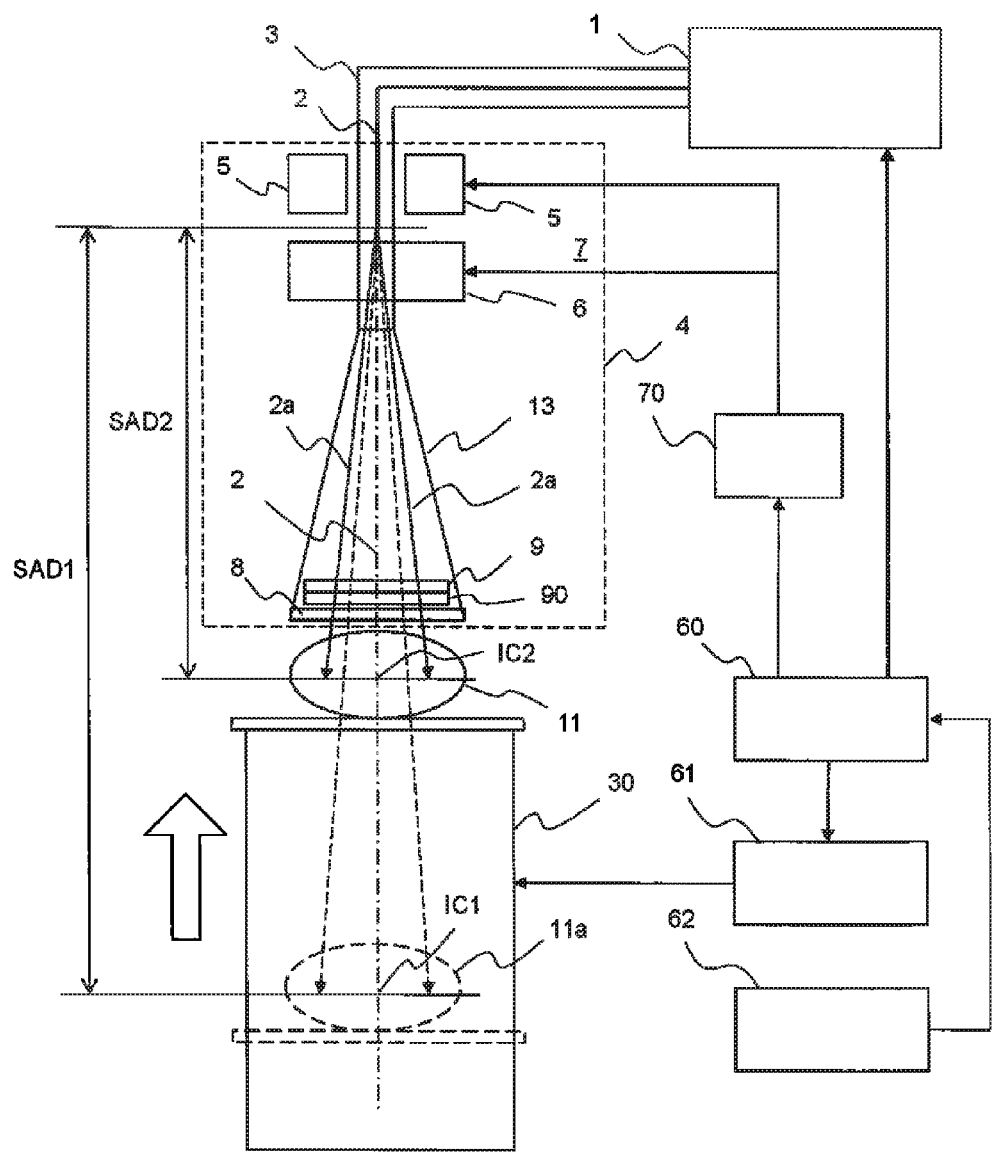
FIG. 1 is a block diagram showing an outline configuration and operation of particle beam therapy system according to this invention.

FIG. 1 is a schematic diagram showing an outline of particle beam therapy system according to EMBODIMENT 1 of this invention. A particle beam 2 which is extracted as a high energy beam from an accelerator 1 for accelerating a charged particle beam passes through a vacuum duct 3 and is transported to an irradiation nozzle 4 which is provided in the downstream side of the vacuum duct 3. Here, bending electromagnets for changing a travelling direction of the particle beam 2 are provided at parts where the vacuum duct 3 is bent, however, in FIG. 1, the bending electromagnets are omitted. In the irradiation nozzle 4, the particle beam 2 is scanned in two-dimensional direction which is perpendicular to a travelling direction of the particle beam 2 by a scanning electromagnet 7 comprising an X-direction scanning electromagnet 5 and a Y-direction scanning electromagnet 6. A particle beam 2a which is scanned passes through a downstream vacuum duct 13 and comes out to the atmosphere from a beam outlet window 8 so as to irradiate a patient 11, which is an irradiation object, who is placed on a treatment table 30. Various kinds of irradiation parameters including an irradiation distance are set in a treatment planning unit 62. Parameters for irradiating with the irradiation parameters are transmitted from the treatment planning unit 62 to an irradiation control unit 60, and each instruction is outputted from the irradiation control unit 60 to a treatment table control unit 61, the accelerator 1 and a scanning electromagnet power source 70.

In a particle beam therapy system, generally, an isocenter which is reference of a position for irradiating is set. An isocenter is generally set at one position which is characteristic position of equipment. That is, an isocenter is generally set on a central axis of a particle beam and at a position which is center of a particle beam irradiation. In FIG. 1, a position indicated by IC1 is an equipment isocenter which is peculiar to equipment. Like a patient 11a indicated by a broken line, generally, a patient is positioned so as to make the position IC1 to be reference position of an affected area of a patient, and then the patient is irradiated with a particle beam. However, an equipment isocenter IC1 is generally distantly-positioned to some extent from the beam outlet window 8 and while a particle beam travels in the atmosphere, a beam diameter of the particle beam is enlarged by scattering. Further, there are also factors of scattering in members through which a particle beam passes, such as the beam outlet window 8, a beam position monitor 9 which is generally provided in the downstream vacuum duct 13, and a dose monitor 90.

Figure 2:
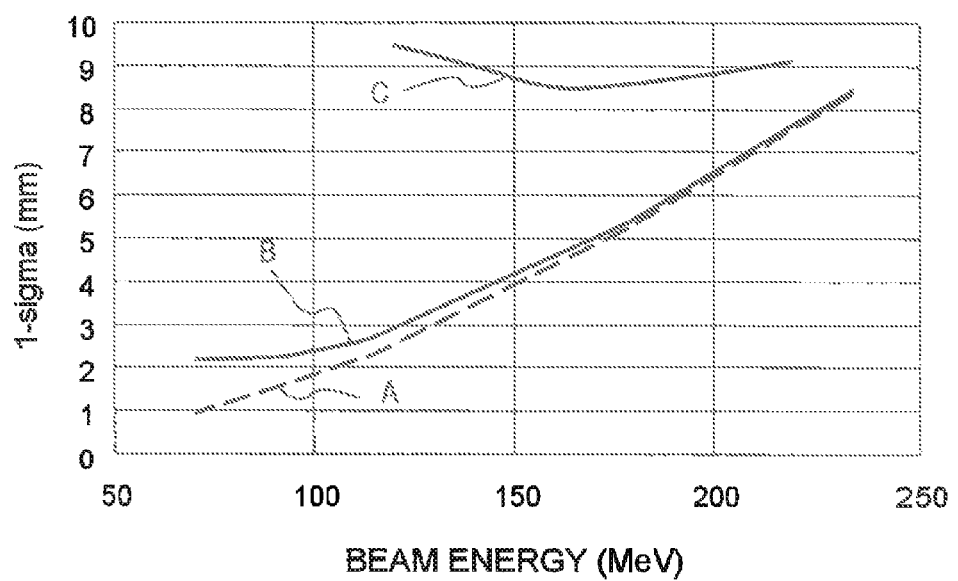
FIG. 2 is a diagrammatic view showing an example of advantage of this invention.

A scanning irradiation method is one of three-dimensional irradiation methods, has a high degree of freedom of irradiation and can be applied to an affect part which has a complicated shape. On the other hand, head and neck comprises many important internal organs such as eyeball, optic nerve, spinal cord, brain, etc., therefore, there is a great need for a scanning irradiation method to be applied to treatment for head and neck. However, in a case of head and neck, unlike the trunk, the size is small, therefore, a depth to an affect area is comparatively shallow and further, and a level of necessary energy of a beam is low. FIG. 2 shows a beam size at a position of a range of each energy in a case where a particle beam enters in a water phantom. As a level of energy of particle beam increases, a range increases, and a particle beam travels for a long distance in water, therefore, a beam size of the particle beam is increased by scattering. A broken line A in FIG. 2 shows a beam size of physical limits caused by scattering of the water. Further, a solid line B shows a beam size at a position in the water in a case where a distance from a vacuum outlet window to water surface is approximately 0.8 m, as one example of technology of this invention. Further, a solid line C shows a beam size at a position in the water in a case where a distance from a vacuum outlet window to water surface is approximately 3 m, as one example of conventional technology.

In a case of proton of 150 MeV, when loss such as a vacuum window, a monitor, the atmosphere, etc. is ignored, there is a range of approximately 16 cm and in a case of head and neck, in many cases, a range is less than 16 cm. That is, when a case is took into consideration, a beam which has energy lower than 150 Mev shown in FIG. 2 and has a small diameter is required. However, in a case of conventional technology in which a travelling distance in the atmosphere is large, when a beam has energy which is lower than 150 MeV, contribution of a scattering (angle) which is caused by a vacuum window or a monitor or the atmosphere before a particle beam reaches a patient, is large, therefore, a beam diameter of a particle beam is extremely large.

Consequently, in this invention, in order not for a beam diameter of a particle beam in an affected area of a patient to be enlarged by scattering, when a particle beam irradiates the affected area of the patient, the patient is moved to a position which is close to the beam outlet window 8 and then a particle beam irradiates the patient. By irradiating a particle beam as above-mentioned, as shown by a solid line B in FIG. 2, a particle beam can irradiate an affected area with a beam size which is close to be a size of physical limitation caused by scattering of water, which can not be physically avoided. In this case, a position which is not an equipment isocenter IC1 is set as an isocenter as reference position when irradiation is performed, that is, as an irradiation isocenter IC2. Irradiation parameters for irradiating at a position which is not the equipment isocenter IC1 are set in the treatment planning unit 62, for example. Here, a distance from a center position at which a particle beam is bent by deflecting with the scanning electromagnet 7, that is, deflection center to isocenter as a center of an irradiation object is referred to as an irradiation distance (SAD: Source Axis Distance). As shown in FIG. 1, conventionally, an irradiation parameter was set as an irradiation distance SAD1 from a deflection center to an equipment isocenter IC1, however, in this invention, irradiation parameters are set on the condition where an irradiation distance is set as SAD2 which is shorter than SAD1.

As described in the above, conventionally, when a particle beam is irradiated, the equipment isocenter IC1 is commonly a reference position. However, according to this invention, the above-mentioned idea is abandoned, and novel idea, that is, irradiation is performed not at a position of an equipment isocenter IC1, but at a position which is closer to a beam outlet window, is introduced. The above-mentioned is a great point of this invention.

Figure 3:
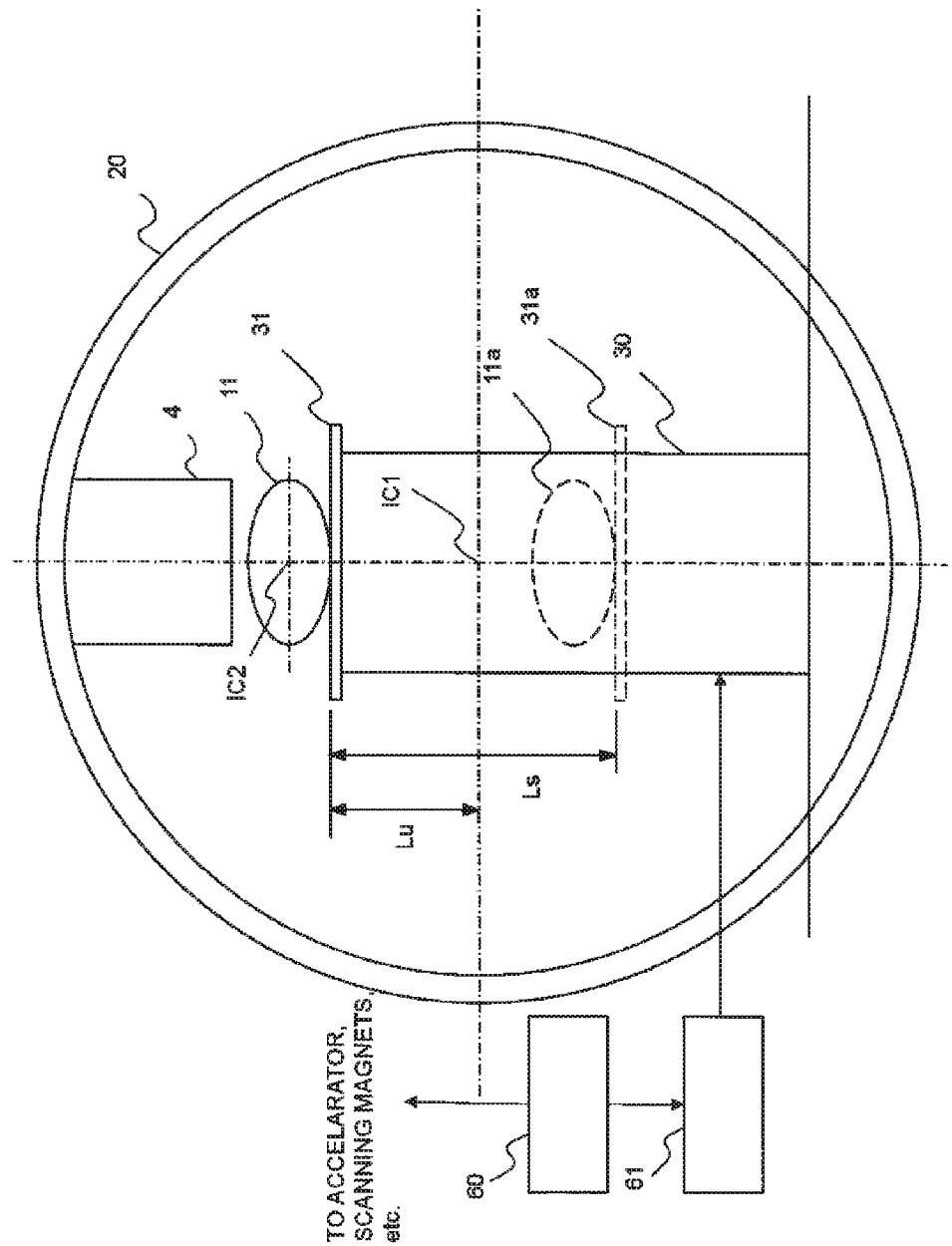
FIG. 3 is a schematic block diagram showing a principal part and operation of particle beam therapy system according to EMBODIMENT 1 of this invention.

FIG. 3 is a conceptual diagram showing an irradiation principal unit for applying a gantry type particle beam therapy system to this invention. In FIG. 3, the configuration of the irradiation nozzle 4 is same as that of the irradiation nozzle 4 in FIG. 1. Generally, in a gantry type particle beam therapy system, an equipment isocenter IC1 is positioned at a point where a rotary center axis of a gantry body 20 and a scanning center axis of a particle beam intersect with each other. Here, a scanning center axis of a particle beam is a center axis of a particle beam which passes in a case where the scanning electromagnet 7 is not powered, that is, the particle beam 2 is not deflected. The above-mentioned point is determined uniquely and peculiarly to equipment, and is convenient as a reference position for irradiating a particle beam. Therefore, conventionally the above-mentioned point has been set as an isocenter. A patient is placed on a top panel 31 of the treatment table 30 (will be referred to as a treatment table panel 31), a reference position of an affected area which is an irradiation object (hereinafter, will be referred to as a patient isocenter) is positioned so as to match with an isocenter IC1. Further, the treatment table 30 can be moved by a large stroke Ls so as for a patient who is placed on the treatment table panel 31 to be able to move close to the irradiation nozzle 4. By controlling the treatment table 30 according to a position of the treatment table when the treatment table 30 is positioned and data which is stored in the treatment planning unit 62 by the treatment table control unit 61, a patient who is placed on the treatment table panel 31 is positioned at a predetermined position.

Figure 4:
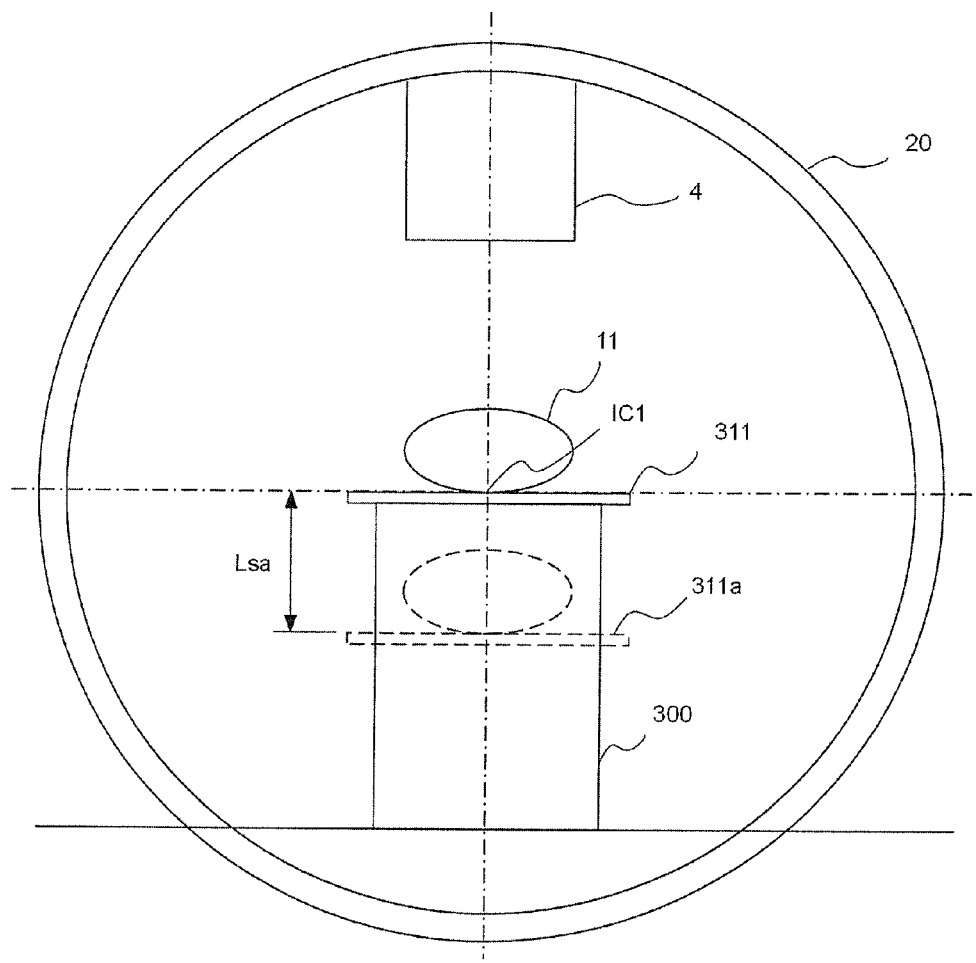
FIG. 4 is a schematic block diagram showing a principal part of conventional particle beam therapy system.

FIG. 4 is a diagram showing an outline of conventional gantry type particle beam therapy system. As shown in FIG. 4, according to a conventional treatment table 300, a treatment table panel 311 can be moved from a position of the treatment table panel 311a which is indicated by a dotted line, that is, a position when a patient 11a is placed, to a position of an equipment isocenter IC1 at most by a stroke Lsa. That is, conventionally, a patient isocenter only needed to be positioned at the equipment isocenter IC1. Therefore, it is not necessary for the treatment table panel 311 to be moved over a position of the isocenter IC1.

As can be seen clearly comparing FIG. 4 describing a conventional particle beam therapy system and FIG. 3 describing a particle beam therapy system according to this invention, a stroke Ls, by which the treatment table panel 31 of the treatment table 30 can be moved, is larger than a stroke Lsa, by which the treatment table panel 311 of the conventional treatment table 300 can be moved, by Lu. Thereby, an irradiation object which could not be approached to the irradiation nozzle 4 in the past can be approached to the irradiation nozzle 4. By introducing a novel idea, that is, irradiating an irradiation object at a position which is not a position of the equipment isocenter IC1, an irradiation object can be approached closer to the irradiation nozzle 4 in comparison with conventional particle beam therapy system.

Figure 5:
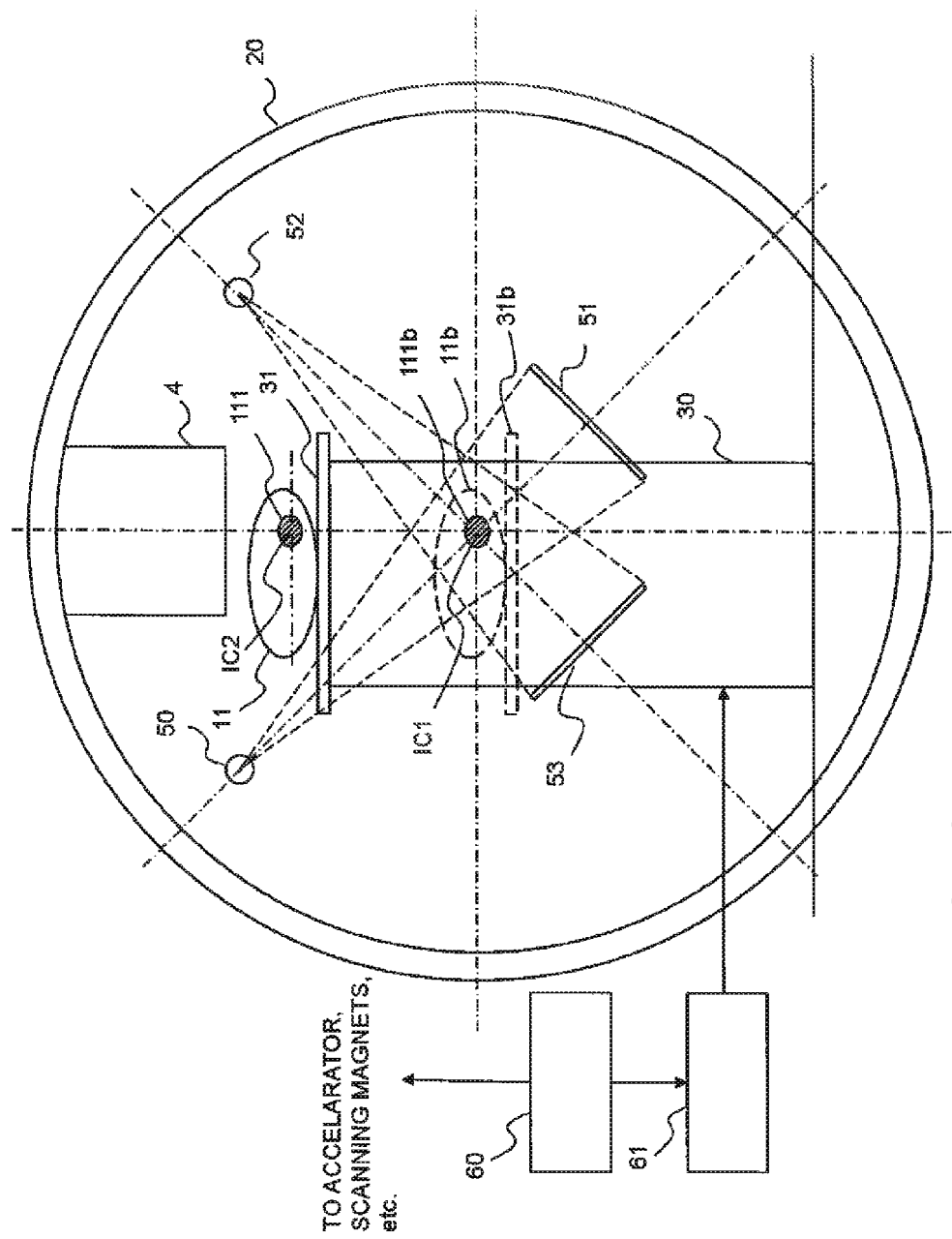
FIG. 5 is a schematic block diagram showing a principal part and operation of another particle beam therapy system according to EMBODIMENT 1 of this invention.

One example of positioning of a patient in particle beam therapy system according to EMBODIMENT 1 of this invention will be described based on FIG. 5. An X-ray tube 50 extracts an X-rays to an affected area 111b of a patient 11b, an X-ray image of the patient 11b is imaged by an X-ray image receiving equipment 51. In the same way, an X-ray tube 52 which is provided at a position which is different from that of the X-ray tube 50 radiates an X-ray to the affected area 111b of the patient 11b, an X-ray image of the patient 11b is imaged by an X-ray image receiving equipment 53. Based on the above-mentioned X-ray images which are imaged from two directions, a position of a patient isocenter as a center of the affected area, which is set in the affected area 111b in advance, is specified. By moving the treatment table 30, a patient is moved vertically, and from front to back and from side to side, a position of the patient isocenter is controlled so as to match with the equipment isocenter IC1. After the patient isocenter is matched with the equipment isocenter IC1, in order for the patient isocenter to be a position of the irradiation isocenter IC2, the treatment table 30 is controlled for the treatment table panel 31 to be elevated to a position which was set in advance.

Figure 6:
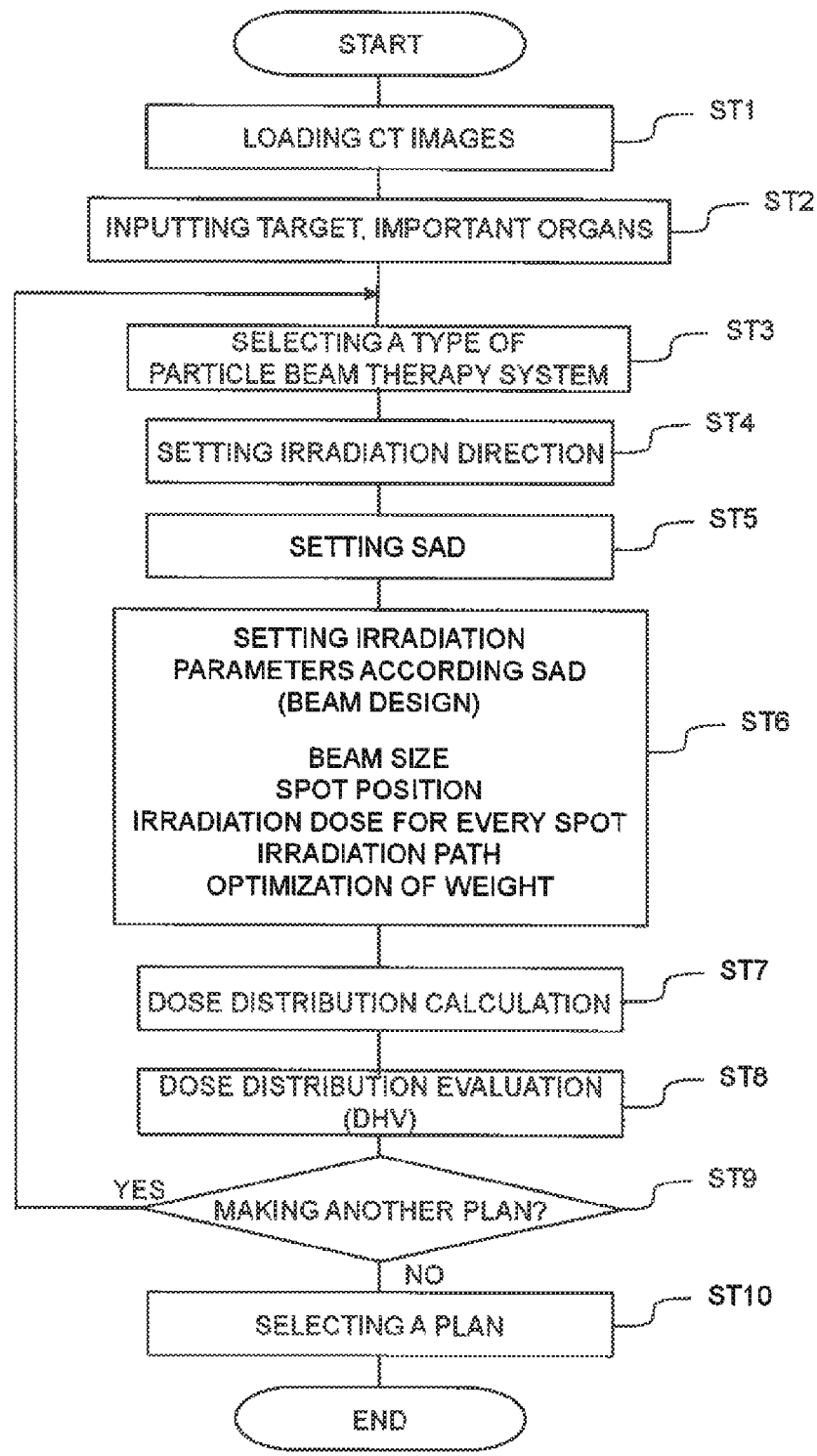
FIG. 6 is a flowchart showing operation of particle beam therapy system according to EMBODIMENT 1 of this invention.

Here, a treatment plan of particle beam therapy system according to this invention is described. FIG. 6 is a flowchart describing a treatment plan. First, CT images such as an X-ray CT including an affected area of a patient are loaded (ST1). Referring to data of the CT images, an irradiation region (target) or important organs are inputted (ST2). Based on the target and arrangement of important organs, a type of particle beam therapy system such as gantry-type is selected (ST3). After the type of particle beam therapy system is selected, an irradiation direction of a particle beam is set (ST4). After the irradiation direction is set, according to the irradiation direction, an irradiation distance SAD is set (ST5). Here, according to conventional particle beam therapy system, a SAD is a distance which was determined in advance based on positional relation of an irradiation nozzle and an equipment isocenter. However, according to particle beam therapy system of this invention, a SAD is not a determined distance, and based on a patient, an affected area, an irradiation nozzle or an irradiation direction, a SAD is determined for every treatment plan so as for an affected area to be close to an irradiation nozzle as much as possible.

When a SAD is set, according to a value of the SAD, a beam design is performed (ST6). A beam design is performed by determining a beam size, a spot position, irradiation dose for every spot, an irradiation path (moving path of a spot), optimization of weight, etc. When irradiation parameters are set by the beam design, a dose distribution calculation is performed by using these parameters (ST7), and a dose distribution evaluation (dose volume histogram) (DVH: Dose Volume Histogram) is performed (ST8). Generally, in many cases, a plan of multi-port irradiation (irradiation is performed from a plurality of irradiation directions) is made, and further, in many cases, a plurality of plans are made and compared. Consequently, it is judged whether it is necessary to make another plan or not (ST9). In a case where it is judged such that it is necessary to make another plan, the system returns to the step ST3 and another plan is made. In a case where it is judged such that it is not necessary to make another plan, a treatment plan which is applied to a treatment is selected from the treatment plans which were made (ST10).

Data such as irradiation parameters of the selected treatment plan are stored in the treatment planning unit 62. In performing irradiation, an instruction for irradiation with the irradiation parameters which are stored in the treatment planning unit 62 is transmitted from the treatment planning unit 62 to the irradiation control unit 60, and each instruction is outputted from the irradiation control unit 60 to the treatment table control unit 61, the accelerator 1, a scanning electromagnet power source 70, etc. respectively.

As above-mentioned, according to particle beam therapy system of EMBODIMENT 1 of this invention, the affected area 111, which is an irradiation object, is approached to the irradiation nozzle 4, and according to the state where the affected area 111 is close to the irradiation nozzle 4, that is, SAD of a small value, a treatment plan is performed, an instruction based on irradiation parameters which are stored in the treatment plan unit 62 is outputted from the irradiation control unit 60 to the accelerator 1, the scanning electromagnet power source 70, the treatment table control unit 61, etc. so as to irradiate a particle beam. By performing the above-mentioned, an influence of enlargement of a beam diameter which is caused by scattering while a particle beam travels in the atmosphere can be decreased. In addition to the above, an influence of enlargement of a beam diameter which is caused by scattering by a member such as the beam outlet window 8 of an irradiation nozzle, the beam position monitor 9, the dose monitor 90, etc. can be decreased, therefore, a beam diameter of a particle beam in the affected area 111 can be made smaller than that of conventional particle beam therapy system. Consequently, an influence to surrounding organs can be decreased, and a particle beam treatment with a high precision can be performed.

Embodiment 2

Figure 7:
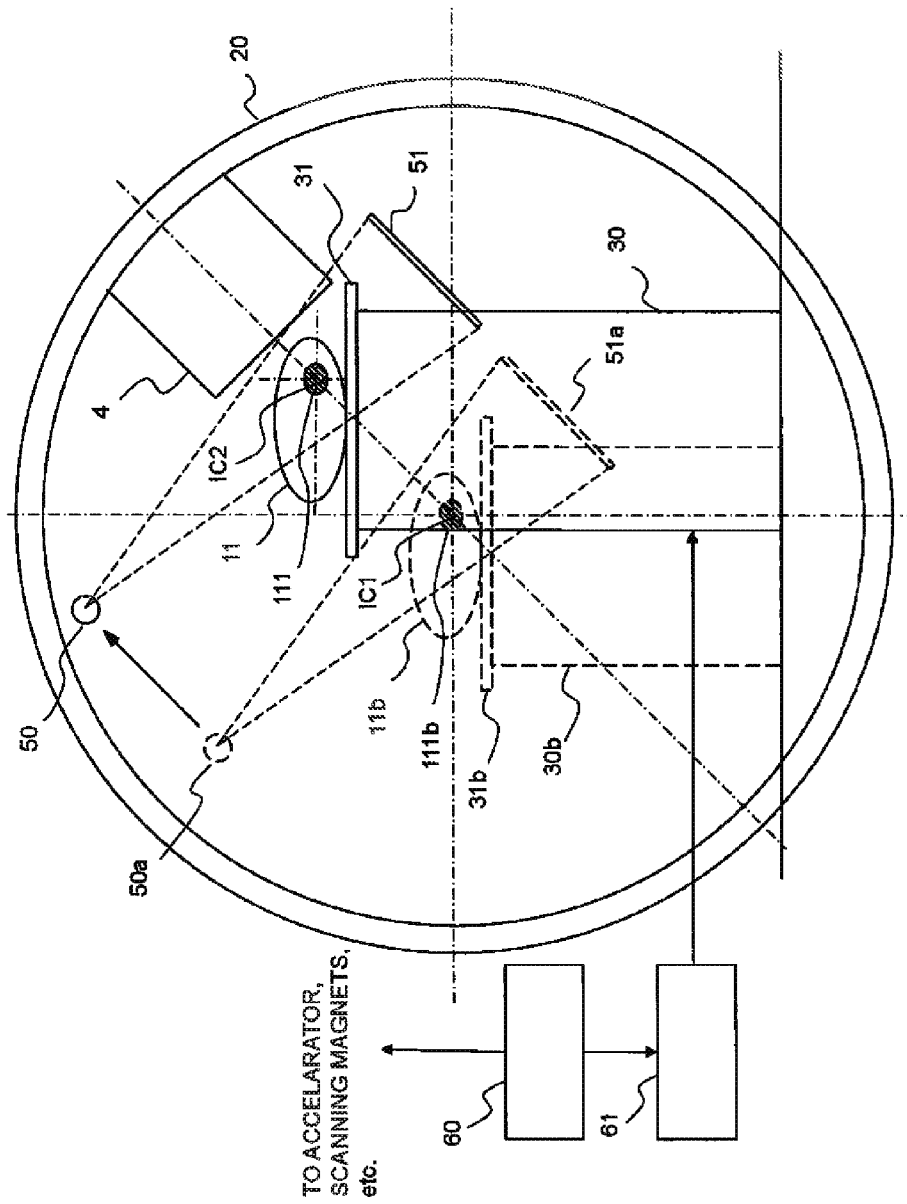
FIG. 7 is a schematic block diagram showing a principal part and operation of particle beam therapy system according to EMBODIMENT 2 of this invention.

FIG. 7 is a sectional side schematic diagram showing an outline of a principal part and operation of particle beam therapy system according to EMBODIMENT 2 of this invention. In FIG. 7, the same reference character as that in FIG. 5 shows the same or a corresponding part. In some cases of an affected area, it is convenient to irradiate the affected area with a particle beam from an oblique direction. The irradiation angle is set in step ST6, which was described in EMBODIMENT 1, for example. In a case where a particle beam is irradiated from an oblique direction, by rotating a gantry body 20 as shown in FIG. 7, an irradiation nozzle 4 is set to an oblique direction of a patient so as to irradiate the patient with a particle beam. In this case, first, by an X-ray image of an X-ray receiving equipment 51 during a position alignment, a position of a treatment table 30 is controlled to set at a position of a treatment table 30b shown in FIG. 7 so as for a patient isocenter which is a reference position of an affected area 111b of a patient 11b during position alignment to match with an equipment isocenter IC1. Further, in the same way as shown in FIG. 5 of EMBODIMENT 1, positioning may be performed by two images using two X-ray tubes and two pieces of X-ray receiving equipment. After that, the treatment table 30 is moved so as for a value of SAD to be a set value, an X-ray tube 50a and an X-ray receiving equipment 51a is also moved by a distance between the equipment isocenter IC1 and an irradiation isocenter IC2, a position of the treatment table 30 is set for a position of a patient isocenter of an affected area 111 of a patient 11 after being moved to be a position of the irradiation isocenter IC2.

As above mentioned, even in a case where an irradiation of a particle beam is set to be performed from an oblique direction, by approaching the affected area 111 which is an irradiation object to the irradiation nozzle 4 so as for a value of a SAD to be set smaller than normal value of a SAD, positioning set is performed. In this case, it is preferable such that the X-ray tube 50 and the X-ray receiving equipment 51 for monitoring a position of the affected area 111 are moved by a distance between the equipment isocenter IC1 and the irradiation isocenter IC2, and a position of the affected area 111 is monitored, and fine adjustments are made so as the patient isocenter of the affected area 111 to match with the irradiation isocenter IC2. Further, it is not needless to say such that in a case where the treatment table 30 is only elevated as described in EMBODIMENT 1, the X-ray tube 50 and the X-ray tube receiving equipment 51 may be moved by a distance between the equipment isocenter IC1 and the irradiation isocenter IC2, a position of the affected area 111 may be monitored, and fine adjustments may be made so as for a patient isocenter to match with the irradiation isocenter IC2.

As above mentioned, according to a particle beam therapy system according to EMBODIMENT 2 of this invention, even in a case where irradiation is performed from an oblique direction, the affected area 111 which is an irradiation object is approached to the irradiation nozzle 4, and according to the state where the affected area 111 is close to the irradiation nozzle 4, that is, a small value of a SAD, a treatment plan is performed. By performing the above-mentioned, an influence of enlargement of a beam diameter which is caused by scattering while a particle beam travels in the atmosphere can be decreased. In addition to the above, an influence of enlargement of a beam diameter which is caused by scattering by a member such as the beam outlet window 8 of an irradiation nozzle, the beam position monitor 9, the dose monitor 90, etc. can be decreased, therefore, a beam diameter of a particle beam in the affected area 111 can be made smaller than that of conventional particle beam therapy system. Consequently, an influence to surrounding organs can be decreased, and a particle beam treatment with a high precision can be performed.

Embodiment 3

Figure 8:
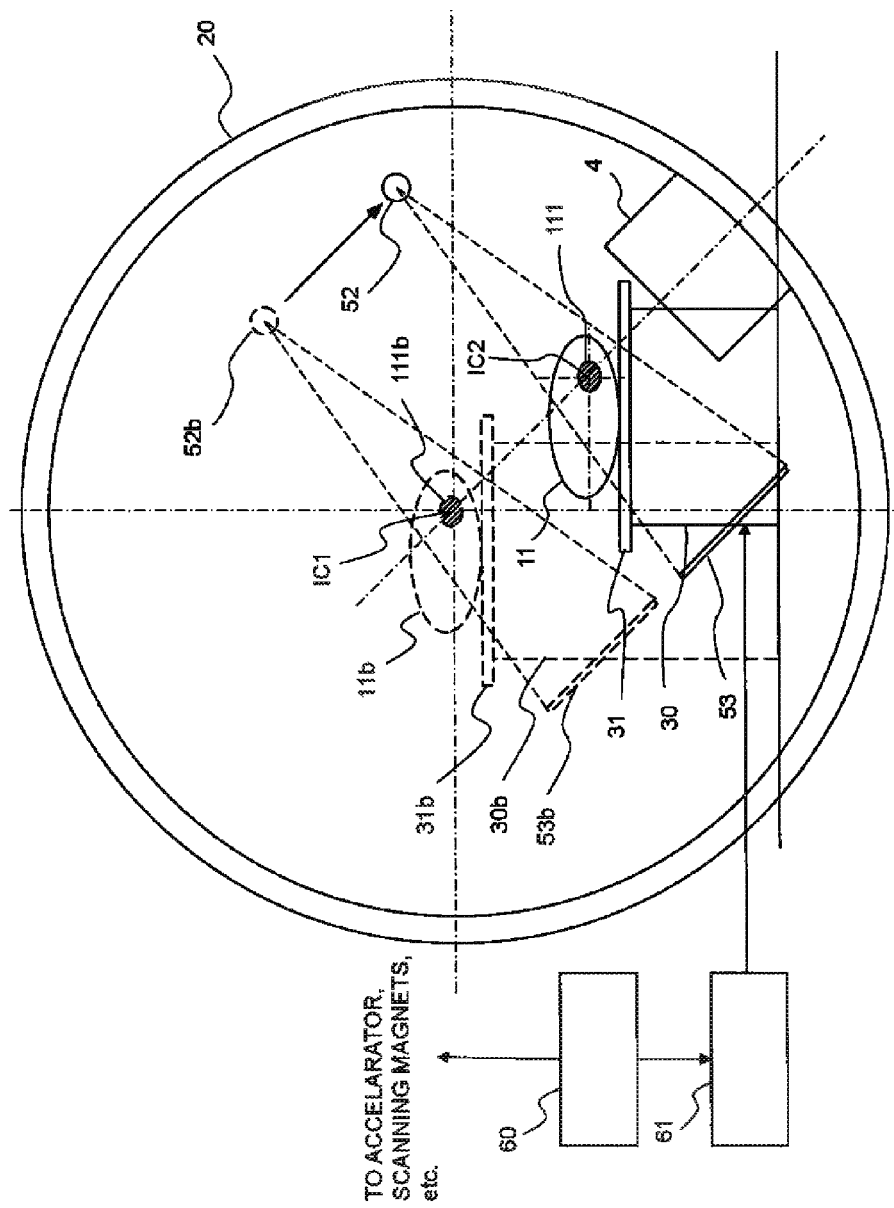
FIG. 8 is a schematic block diagram showing a principal part and operation of particle beam therapy system according to EMBODIMENT 3 of this invention.
Figure 9:
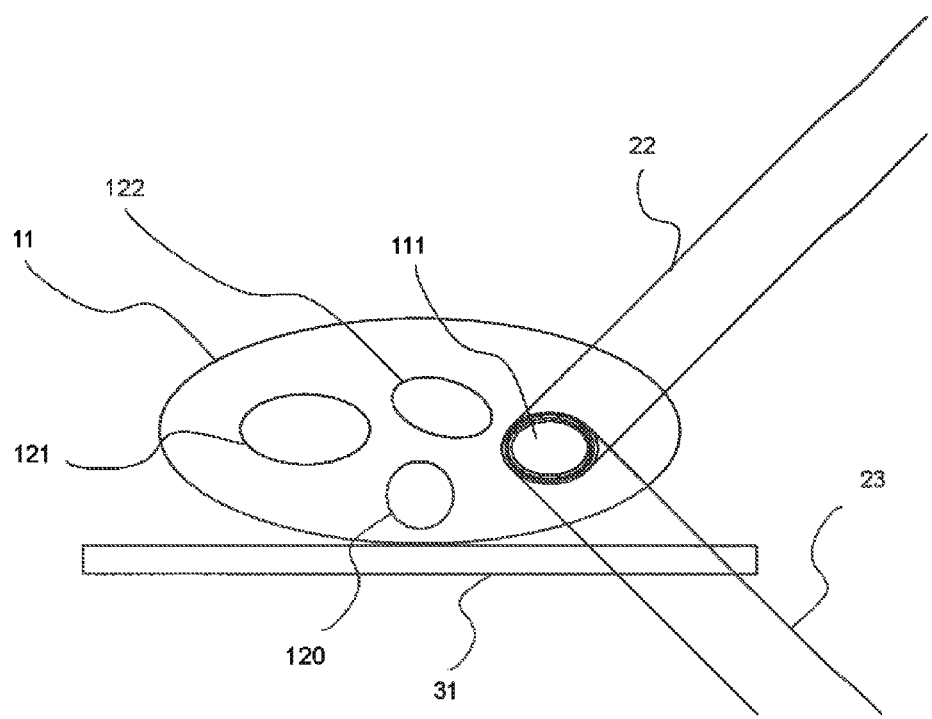
FIG. 9 is an enlarged sectional view showing an example of patient to which particle beam therapy system according to EMBODIMENT 3 of this invention is applied.

FIG. 8 is a schematic block diagram showing a principal part and operation of particle beam therapy system according to EMBODIMENT 3 of this invention. In FIG. 8, the same reference character as that in FIG. 5 or FIG. 7 shows the same or corresponding part. In some cases of an affected area, it is convenient to irradiate an affected area with a particle beam from an obliquely downward. For example, in an enlarged cross-section diagram of a patient 11 shown in FIG. 9, a case, in which an important organ A 120, an important organ B 121, and an important organ C 122, etc. exist in the vicinity of an affected area 111, is assumed. It is supposed that in a treatment plan, it is judged such that it is appropriate to irradiate an affected area with a particle beam from two directions, that is, from a direction of a first irradiation port 22 which is the first direction and from a direction of a second irradiation port 23 which is the second direction. An irradiation from the first irradiation port is performed according to the same procedure as that is described in EMBODIMENT 2, for example. After the irradiation from the first irradiation port is completed, a gantry body 20 is rotated, an irradiation nozzle is set at a position shown in FIG. 8, and an irradiation from the second irradiation port is performed from an obliquely downward. The irradiation from the second irradiation port is performed by moving a patient isocenter of the affected area 111 from a position of an equipment isocenter IC1 to a position of an irradiation isocenter IC2 where a value of a SAD is small, that is, a position which is closer to an irradiation nozzle 4. In order to realize the above mentioned a treatment table can be moved from a position of a treatment table 30*b* to a position of a treatment table 30. Further, it is preferable such that fine adjustments are made by moving an X-ray tube 52 and an X-ray receiving equipment 53 for monitoring a position of the affected area 111 by a distance between the equipment isocenter IC1 and the irradiation isocenter IC2, and monitoring a position of the affected area 111 so as for a reference position of the affected area 111 to match with the irradiation isocenter IC2.

As above mentioned, even in a case where irradiation is performed from an oblique direction, by making a treatment table movable in the same way as that in which an affected area can be approached to the irradiation nozzle 4, a particle beam with less scattering and having a smaller beam diameter can be irradiated onto an affected area.

REMARKS

1: accelerator
2: particle beam
3: vacuum duct
4: irradiation nozzle
5: X-direction scanning electromagnet
6: Y-direction scanning electromagnet
7: scanning electromagnet
8: beam outlet window
9: beam position monitor
11, 11*a*, 11*b*: patient
13: downstream vacuum duct
20: gantry body
30: treatment table
60: irradiation control unit
61: treatment table control unit
62: treatment planning unit
70: scanning electromagnet power source
90: dose monitor
111, 111*b*: affected area
IC1: equipment isocenter
IC2: irradiation isocenter

The invention claimed is:

1. A particle beam therapy system comprising
an accelerator configured to accelerate a charged particle beam so as to extract a particle beam,
a vacuum duct configured to transport the particle beam which is extracted from the accelerator,
an irradiation nozzle which comprises a scanning electromagnet which is provided at the downstream side of the vacuum duct to deflect the particle beam, which travels in the vacuum duct, perpendicular to the direction of travelling so as to scan a patient's affected area which is an irradiation object and a beam outlet window from which the particle beam comes to the atmosphere,
a treatment table configured to place a patient,
a treatment table control unit configured to control a position of the treatment table, and
an irradiation control unit configured to output instructions for controlling the treatment table control unit, the accelerator and the scanning electromagnet,
wherein after the treatment table control unit controls the treatment table so as to move a patient isocenter, which is a reference position of the patient's affected area, to a position of an irradiation isocenter, said irradiation isocenter being set at a position closer to the irradiation nozzle than an equipment isocenter, which is a predetermined characteristic position of the system as reference for positioning, the irradiation control unit outputs instructions for irradiating a patient with the particle beam.

2. The particle beam therapy system as claimed in claim 1 further comprising a gantry body configured to rotate the irradiation nozzle,
wherein the equipment isocenter is set at a center of rotation of the gantry body.

3. The particle beam therapy system as claimed in claim 1 further comprising an X-ray image pickup equipment which comprises an X-ray tube and an X-ray image receiving equipment for positioning a position of a patient,
wherein the X-ray image pickup equipment is moved by a distance between the equipment isocenter and the irradiation isocenter.

4. The particle beam therapy system as claimed in claim 1, wherein after the treatment control unit controls the treatment table so as for the patient isocenter to match with the equipment isocenter, the treatment control unit controls the treatment table so as for the patient isocenter to match with the irradiation isocenter.

* * * * *